United States Patent [19]

Lazzara, Jr.

[11] Patent Number: 6,004,131
[45] Date of Patent: Dec. 21, 1999

[54] BLOCKED TUBE FOR BRACES AND METHOD OF USE

[76] Inventor: Gasper Lazzara, Jr., 129 Bristol Pl., Ponte Vedra Beach, Fla. 32082

[21] Appl. No.: 09/270,046

[22] Filed: Mar. 16, 1999

[51] Int. Cl.$^6$ ..................................................... A61C 3/00
[52] U.S. Cl. ............................................... 433/17; 433/24
[58] Field of Search .................................... 433/5, 17, 18, 433/24

[56] References Cited

U.S. PATENT DOCUMENTS

| | | | |
|---|---|---|---|
| 3,335,496 | 8/1967 | Andrews et al. | 433/17 |
| 4,781,582 | 11/1988 | Kesling | 433/17 |
| 5,707,232 | 1/1998 | Strauss et al. | 433/17 |

Primary Examiner—Nicholas D. Lucchesi
Attorney, Agent, or Firm—Whitham, Curtis & Whitham

[57] ABSTRACT

The present invention provides a device and procedure for straightening and leveling of teeth anterior to the molar (chewing) teeth. The procedure utilizes a blocked tube having a channel and an extension and blocking wall. The extension extends from the blocked tube and is substantially parallel to the channel, and the blocking wall extends upward from an end of the extension and is substantially perpendicular to the extension. The blocking wall extends to a same height as the channel with respect to a bottom of the blocked tube. The procedure further uses conventional brackets and wires. The wires are ligated to the brackets and threaded through the channel of the blocked tubes. The wires are cut and contact the blocking wall of the blocked tube.

23 Claims, 3 Drawing Sheets

BLOCKED TUBE FOR BRACES AND METHOD OF USE

BACKGROUND OF THE INVENTION

1. Field of the Invention

The present invention generally relates to an orthodontic device and a procedure using the device for straightening teeth, and more particularly, an orthodontic device and a procedure for straightening teeth anterior to the molar teeth.

2. Background Description

Traditional orthodontic braces are designed to straighten and realign teeth in order to improve or correct "bite", as well as to correct the esthetic appearance of one's teeth. These traditional braces typically are applied to both front teeth (e.g., first and second bicuspids, cuspids and lateral and central incisors) and back teeth (e.g., molars and chewing teeth) and straighten one's teeth typically within 2–3 years. The use of traditional orthodontic braces is relatively expensive, and mostly used on children.

In order to maintain the beneficial effects of the orthodontic procedures, patients must wear "retainers" once the orthodontic braces are removed. However, many patients do not wear these retainers and their teeth thus shift and gradually lose their alignment. Thus, over time, the benefit gained from using traditional orthodontic devices (e.g. straight teeth) is lost.

Currently, in order to re-straighten one's teeth, traditional orthodontic braces must be again applied, which consists of a considerable reinvestment of one's time and energy. Also, many persons who do not have severe orthodontic cosmetic defects, but merely require cosmetic straightening of their teeth, would also need to undergo the traditional straightening of teeth, which is time consuming.

Thus, it would be beneficial to have available an orthodontic device and technique that, in a relatively short period of time, could restore the cosmetic benefits of an earlier traditional procedure, without having to reinvest the considerable time and energy associated with traditional braces. Also, it would be beneficial is this same procedure could be used to straighten teeth for persons who have not previously undergone the traditional procedure.

SUMMARY OF THE INVENTION

The invention is directed to a blocked tube used with conventional braces for the rapid orthodontic straightening of the teeth anterior to the molar or "chewing" teeth. The blocked tube includes a base with a hollow channel extending through it, such that arch wires of the braces can be threaded through the channel. A blocking wall is positioned on the blocked tube so that the distal ends of the arch wires, after being threaded through the channel, contact the blocking wall.

The invention is further directed to an orthodontic procedure using the blocked tube of the present invention. In the procedure, the blocked tube is attached to a tooth immediately posterior to the teeth to be straightened on both sides of the mouth. Conventional brackets are applied to the teeth to be straightened and heat-activated arch wires are attached to the brackets. The ends of the arch wires are threaded through the channel of the blocked tube and are cut so as to contact the blocking wall of the blocked tube. This contact creates an accelerated moment of force against the teeth to be straightened, thus expediting the movement of the teeth to the desired position.

DETAILED DESCRIPTION OF THE DRAWINGS

DETAILED DESCRIPTION OF A PREFERRED EMBODIMENT OF THE INVENTION

The present invention is directed to an orthodontic device and method for leveling and aligning teeth anterior to the molar or "chewing" teeth. That is, in preferred embodiments, the device and method of the present invention levels and aligns the first and second bicuspids, cuspids, and lateral and central incisors, in order to improve one's "esthetic smile" in a relatively short period of time. In addition, the device and procedure of the present invention may be used to correct some dimensions of horizontal and vertical overbite, and thus improve corresponding periodontal conditions associated with the correction of these overbites.

Blocked Tube

Figure 1:
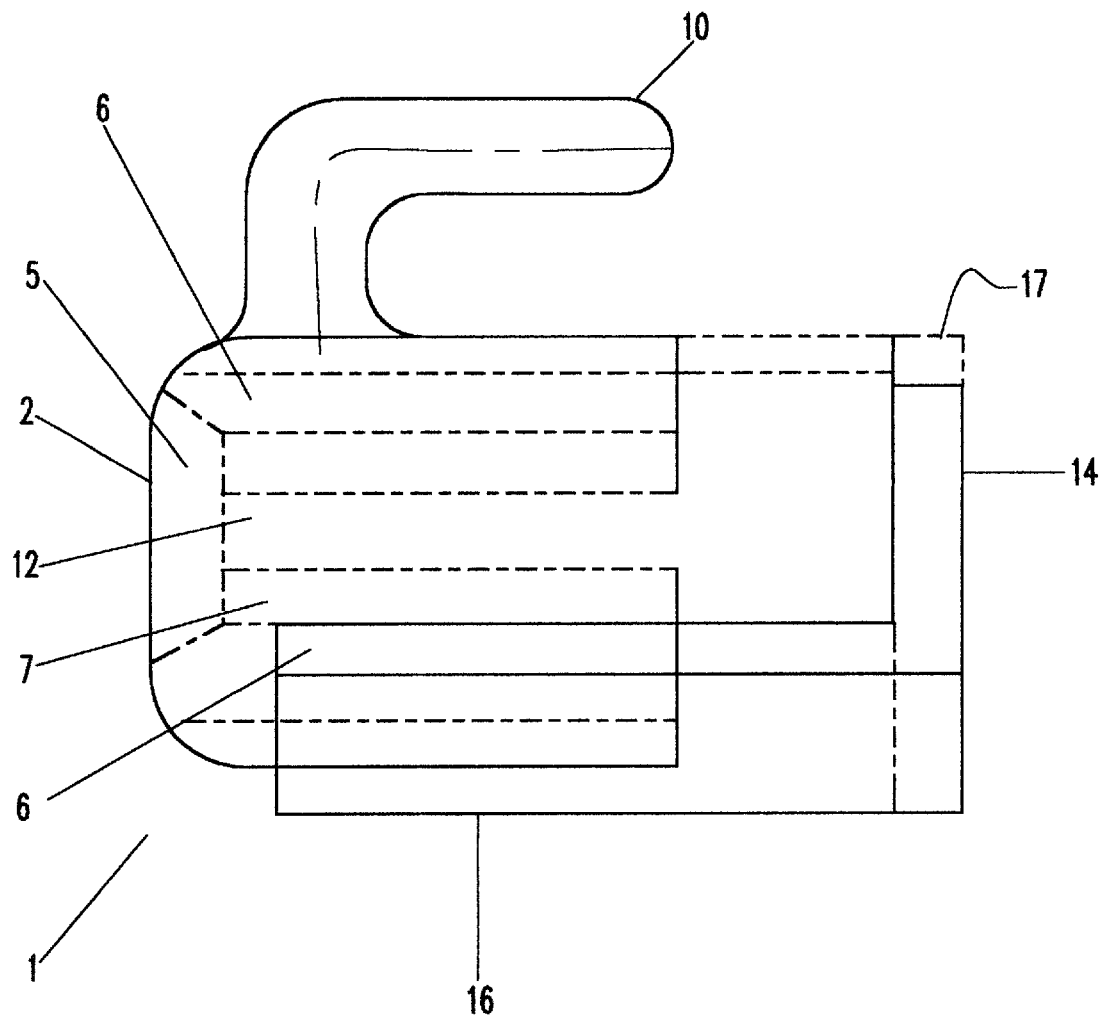
FIG. 1 shows an orthodontic device of the present invention.

Referring now to the drawings, and more particularly to FIG. 1, a blocked tube 1 having a tunnel or channel extending therethrough is shown. Specifically, the blocked tube 1 of the present invention includes a base 2 and a body portion 5 having sidewalls 6 and a top 7. In preferred embodiments, the body portion 5 and the base 2 are integrally attached to one another, and the base 2, sidewalls 6 and top 7 form a tunnel or channel 12 (e.g., hollow center) extending along a length portion of the base 2. The sidewalls 6 may be slanted or perpendicular with respect to the base 2. The integrally formed body portion 5 and the base 2 may simply have a bore therethrough forming the channel 12.

As seen further in FIG. 1, an extension 16 extends from the base 2, and extends substantially parallel to the channel 12. In a preferred embodiment, the extension 16 is approximately 0.145 mm. It is well understood by one of ordinary skill in the art, however, that the length of the extension 16 is not limited to 0.145 mm, but may be any appropriate length and that the length itself of the extension 16 is not critical to the understanding of the present invention.

Referring still to FIG. 1, an arm (e.g., blocking wall) 14 extends upward from the extension 16 so that the extension 16 and the blocking wall 14 are substantially perpendicular to one another. The extension 16 and the blocking wall 14 thus form an L-shaped extension. In a preferred embodiment, the blocking wall 14 extends past the base 2 of the blocked tube 1 by between approximately 0.5 and 2.0 mm; however, other lengths may also be equally used with the present invention. The blocking wall 14 extends upward and preferably corresponds to the height of the channel 12 with respect to a bottom portion of the base 2. The blocking wall 14 may also extend beyond the height of the channel 12 approximately to an upper edge, for example, of the sidewall 6, and an extension 17 (substantially parallel to extension 16) may extend between the blocking wall 14 and the upper edge of the side wall 6 (or vicinity thereof) thereby forming a U-shape. In a perfecting feature of the present invention, a hook 10 extends upward from the base 2.

The base 2 and the body portion 5 (including the sidewalls 6 and top 7) is preferably constructed of stainless steel, but may be constructed of any suitable material, such as ceramic or plastic. Several such appropriate materials are well known and used by those of ordinary skill in the art.

Method of the Present Invention

The method of the present invention includes the use of the blocked tube 1 of FIG. 1 in order to straighten one's teeth. Specifically, prior to using the blocked tube 1 of FIG. 1 and in order to perfect the procedure of the present invention, a complete diagnostic examination of the patient is performed which may include, but is not limited to, cephalometric lateral radiographs, panoramic radiographs, nine intraoral and extraoral photographs.

Prior to applying the blocked tube 1 of FIG. 1, a substantially complete air rotor stripping procedure on all tooth contacts anterior to the first permanent molars is provided. Specifically referring to FIG. 2, air rotor stripping with bur 18 reduces the size of selected teeth in order to create space between the teeth, as necessary. As is well known to one of ordinary skill in the art, tooth reduction through the anterior contacts is somewhat limited by the size and width of the anterior teeth, which may vary from patient to patient. Generally, air rotor stripping will produce a maximum of 8–10 mm of space between teeth to be utilized to straighten the anterior teeth and the bicuspids. These spaces, of course, can vary in size depending on the individual patient and the individual treatment protocol. Also, these reductions are not critical to the understanding of the present invention but are merely provided only if necessary to create appropriate space between the teeth, as determined by an orthodontist or other appropriate professional.

In a preferred embodiment, a Diamond Bur #769T-9XF (SS White Bur) is used to reduce contacts anterior to the first molars and distal to the lateral incisors, and a Diamond Bur #8392-016 (Brassier Diamond Bur) is used to reduce contacts through the anterior contacts. It is noted, however, that the specific burs mentioned above are not critical to the understanding of the present invention, and that any appropriate bur known to one of ordinary skill in the art may be used in order to accomplish the reduction of the patient's teeth.

Figures 2, 3:
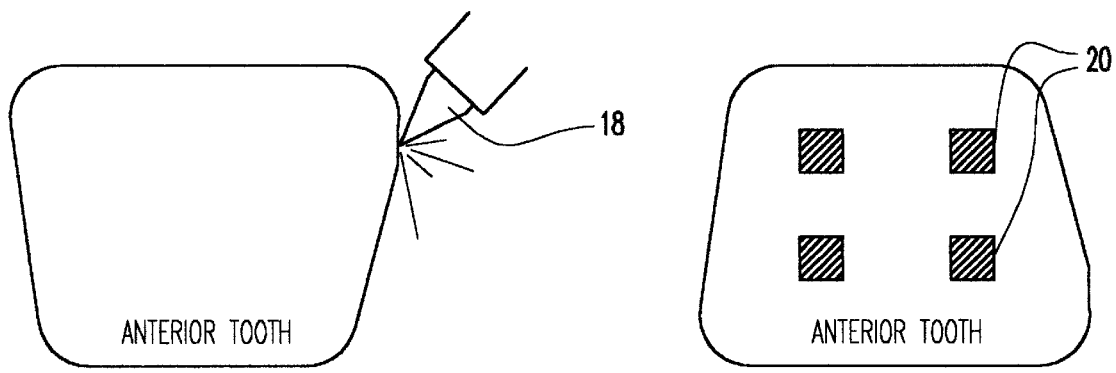
FIG. 2 shows an air rotor stripping procedure.
FIG. 3 shows a conventional bracket mounted on a tooth.

Referring to FIG. 3, a conventional bracket 20 is bonded to one anterior tooth as shown. Preferably 022 mm×028 mm twin edgewise brackets are used; however, other size brackets may also be used depending on the condition of a particular patient's teeth. The brackets 20 may be ceramic, plastic, or metal or other well-known materials used in typical orthodontic procedures, depending on the patient or doctor preference. The brackets 20 are bonded using chemically cured composite, light-cured composite, or light-cured Fuji type cement, or other similar cements known to one of ordinary skill in the art, and which are appropriate for bonding brackets to teeth.

Figure 4:
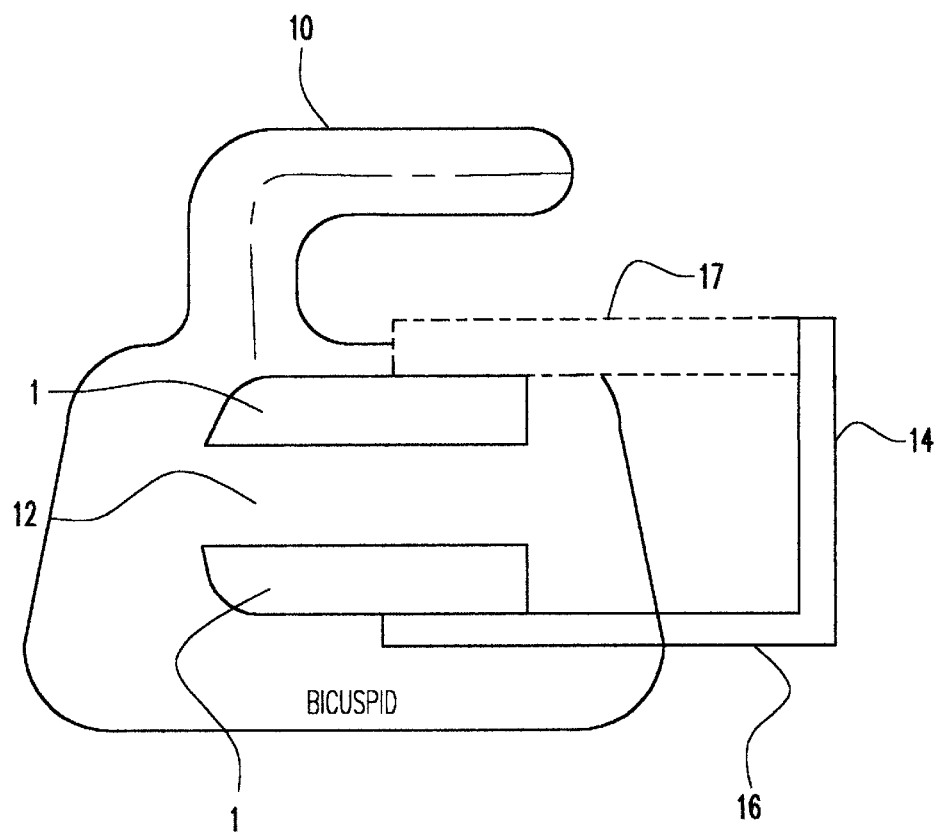
FIG. 4 shows a blocked tube having a channel mounted on a tooth.

Thereafter, the blocked tube I is mounted to each of the four bicuspids, if straightening is required for both upper and lower teeth. FIG. 4 shows the blocked tube 1 mounted to one of the bicuspids. The blocked tube 1 may equally be mounted to the two bicuspids of either the upper or lower teeth, whichever (upper or lower) are being treated. The channel 12 of the blocked tube 1 serves as a conduit and receptacle for the distal ends of the arch wires, and in preferred embodiments, also allows a small end segment (e.g., distal end) to extend from the channel 12 and contact the blocking wall 14. This allows the arch wire to be manipulated during the course of the orthodontic procedure, and protects the patient's mouth from the distal ends of the arch wires. This further maintains arch length and expedites the straightening of a patient's teeth, as discussed below.

In the present invention, each blocked tube 1 is attached to a biscuspid tooth, since, in preferred embodiments, only the teeth anterior to the biscuspids are straightened. However, if the patient has had previous orthodontic treatment and some teeth have been extracted in conjunction with that treatment, then the blocked tube 1 may be bonded to the first molar. In other words, the blocked tube 1 of FIG. 1 should be bonded to whatever tooth is immediately posterior to the teeth that are to be straightened.

Figure 5:
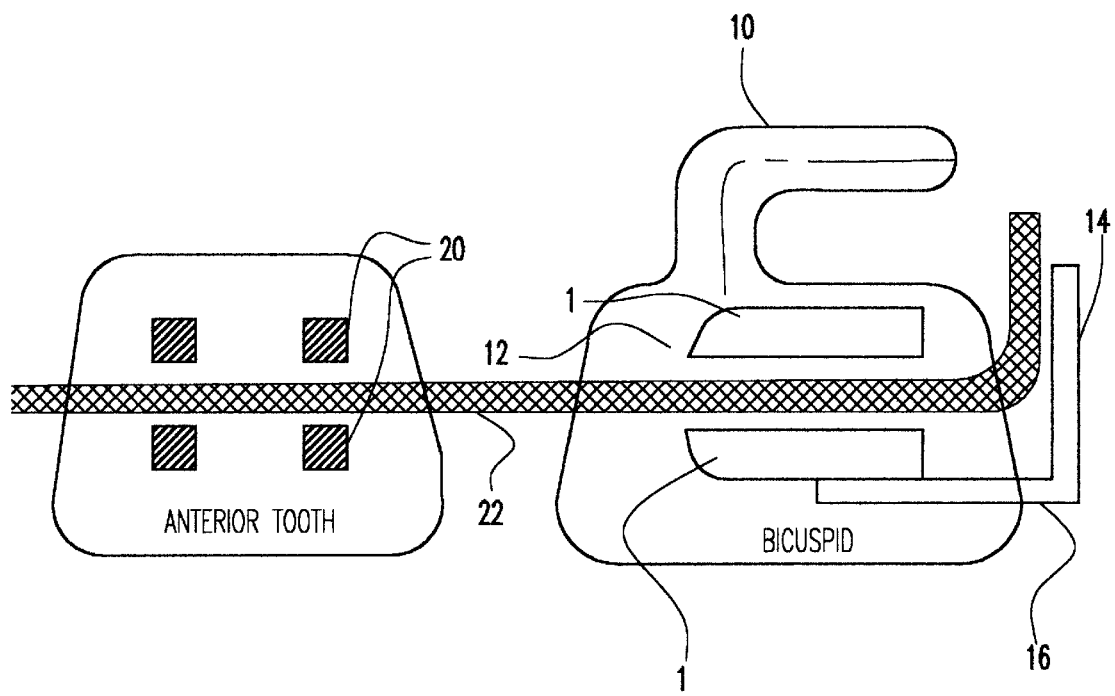
FIG. 5 shows an arch wire mounted on the conventional bracket and threaded through the channel of the blocked tube and past a blocking wall.

Referring to FIG. 5, once the brackets 20 and the blocked tubes 1 are mounted to the patients teeth, an arch wire 22 is ligated to the brackets 20 and threaded through the channel 12 of each blocked tube 1. As seen in FIG. 5, the end of the arch wire extends past the blocking wall 14.

Figure 6:
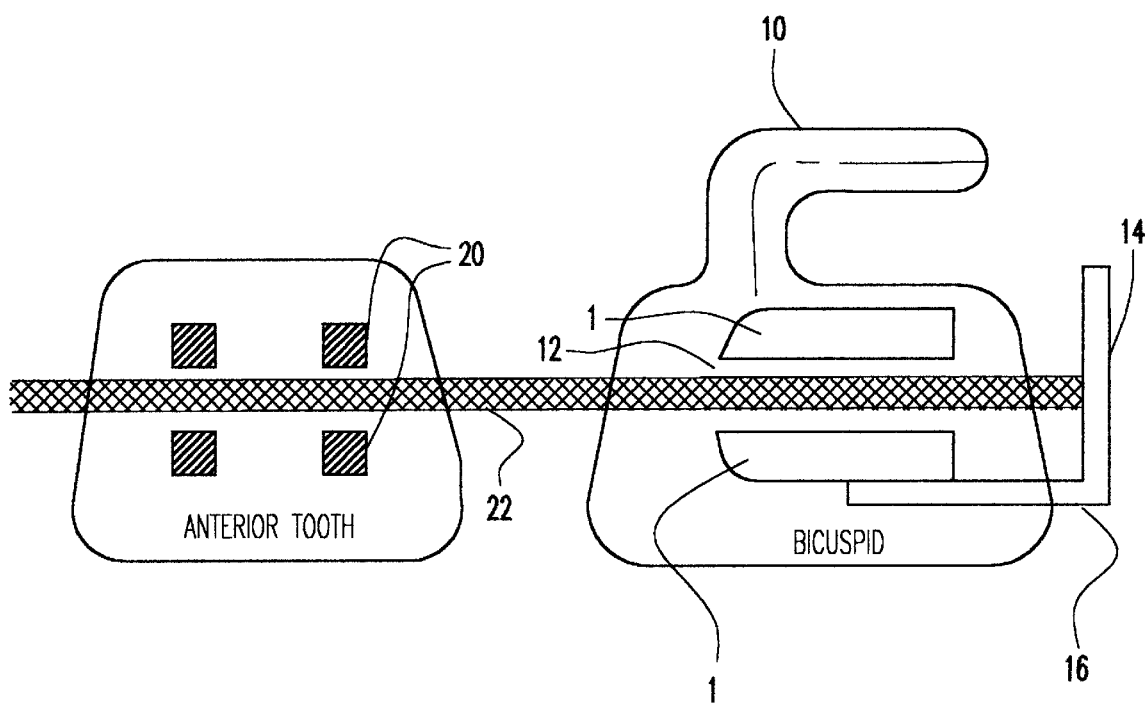
FIG. 6 shows a distal end of the arch wire contacting the blocking wall.

Subsequent to ligating the arch wire 22 around the brackets 20 and through the channel 12 of the blocked tube 1, the arch wire 22 is then cut so that the distal end 24 of the arch wire 22 contacts the blocking wall 14 of the blocked tube 1 (FIG. 6). By adjusting the length of the arch wire 22 (the "arch length") and thus the amount of force being exerted on the blocking wall 14 of each blocked tube 1, the moment of force to the teeth is accelerated. This causes the forces (e.g., compressive and tensile forces) in the arch wire 22 to increase thus causing accelerated movement of the teeth and consequent straightening of the teeth more rapidly than with traditional methods.

In a preferred embodiment, after the arch wires 22 are ligated to the brackets 20 and extended through the channels 12 of the blocked tubes 1, the arch wires are maintained or slightly expanded up to an approximate 2mm arch length. The blocking wall 14 of each blocked tube 1 maintains this arch length. The arch wires 22 are preferably copper-titanium alloy and are heat-activated (e.g., malleable at approximate room temperatures but firm and non-malleable at higher temperatures, such as those found within the mouth). The initial arch wires 22 are preferably 0.016 mm×0.022 mm, however, if the teeth are extremely crowded, the arch wire 22 may be 0.016 mm×0.016 mm or smaller. In instances, 0.018 mm round heat-activated arch wire 22 may be used within the procedure of the present invention. However, the procedure of the present invention may use various other sized arch wires 22 and materials, depending on the particular application and circumstances presented.

In a perfecting feature of the present invention, the arch wires 22 are ligated utilizing elastic ligature that matches bracket 20 and arch wire 22 color. The ligatures are twisted between mesial and distal tie wings in order to achieve maximum seating of the arch wire 22 into the bracket 20.

At subsequent appointments and according to the method of the present invention, religation and implementation of sliding arch corrective mechanics are performed as necessary (typically 2–3 times) to direct further corrective tooth movement, initiate current rotations and space closure, and make midline corrections. Also, the dimensions of the arch wire 22 are stepped up and the composition of the arch wire 22 is altered according to the progress of the straightening procedure. Typically, the arch wire 22 is preferably changed in sequence to (i) 0.0175 mm×0.025 mm nickel-titanium alloy, (iii) 0.018 mm×0.025 mm stainless steel, and (iii) 0.016 mm stainless steel.

Of course religation and implementation of sliding arch corrective mechanics may be performed more or less times, and other dimensions and compositions of the arch wire 22 may be used in order to practice the method of the present invention depending on the preferences of the orthodontist or other professional and the progress of the patient. However, in order to properly practice the method of the present invention, when the subsequent arch wires 22 are ligated to the brackets 20 and threaded through the channel 12 of the blocked tube 1, the distal ends 24 of the arch wire 22 should again contact the blocking walls 14 in order to maintain an appropriate arch length and maximum force on the patient's teeth so as to accelerate the movement thereof.

At the penultimate appointment, all brackets 20 are debonded and removed and final esthetic recontouring for optimal "smile" results is performed. In one embodiment, a light-activated tooth whitening procedure is completed, and nightwear trays to augment the whitening procedure are fabricated. Clear plastic retainers may also be fitted at this time. X-rays may also be taken in order to determine if any pathology and/or abnormalities are present, such as root resorbtion. The number of appointments needed to carry out the procedure of the present invention will vary from patient to patient, and the total time typically extends for approximately 6 months.

Example of Treatment Protocol Using the Method of the Present Invention

The following is just one example of the method of the present invention. This illustrative example includes twelve appointments. However, it is well understood by one of ordinary skill in the art that more or less than twelve appointments may be necessary to perfect the method of the present invention, and that the use of twelve appointment is for illustration only.

It is also well understood by one of ordinary skill in the art that each appointment is not limited to the specific procedures performed during each appointment period. In fact, more or less of these procedures may be performed during each appointment depending on the progress being made by each individual patient. Accordingly, and for example, a patient may not have to have the arch wire 22 removed and stepped up during any one of the appointments, but may have some other procedure(s) performed depending on the professional judgement of the orthodontist or other professional.

However, as noted above, it is important to the preferred embodiment of the present invention that the arch wires 22 threaded through the channels 12 of each of the blocked tubes 1 contact the blocking walls 14. This maintains the arch length and also expedites the straightening of the patient's teeth. Thus, what is critical to the present invention is that the distal ends 24 of the arch wires 22 substantially maintain contact with the blocking wall 14 of the blocked tubes 1 substantially during and after rewiring of the orthodontic device in order to expedite the straightening procedure.

First Appointment

The first appointment includes air rotor stripping and applying the brackets 20 and blocked tubes 1 to the patient's teeth, as described above in detail. Arch wires 22 are then ligated to the brackets 20 and threaded through the channels 12 of the blocked tubes 1. The arch wires 22 are cut so that the distal ends 24 of the arch wires 22 contact the blocking walls 14.

Second Appointment

At the second appointment, all rotations are religated. Sliding arch mechanics with elastic chains are utilized to direct corrective tooth movement, initiate current rotations, space closure and make midline corrections.

Third Appointmnent

Larger dimension nickel-titanium alloy arch wire 22 is utilized for both upper and lower arch wires 22 whenever possible, for example 0.016 mm×0.022 mm or 0.0175 mm×0.025 mm. The arch wires 22 are ligated with twisted elastic ligatures to achieve maximum arch wire 22 to bracket 20 engagement. The arch wire 22 length is adjusted to maintain or expand arch length as the case demands by utilizing the blocked tube 1 of the present invention.

Fourth Appointment

The arch wire 22 dimension is stepped up to 0.017 mm×0.025 mm nickel-titanium alloy, as necessary. All rotations are religated with twisted elastic ligatures which utilize sliding arch mechanics with elastic chains to direct corrective tooth movement, rotations, space closure and midline corrections.

Fifth Appointment

Religation and implementation of sliding arch corrective mechanics are carried out at this time. The arch wire 22 dimension is stepped up to 0.0175 mm×0.025 mm nickel titanium alloy as necessary.

Sixth Appointment

The upper and lower arch wire 22 dimension is stepped up to 0.018 mm×0.025 mm stainless steel alloy. The blocked tube 1 of the present invention is utilized to maintain or expand arch length as necessary, together with ligation with twisted elastic ligatures.

Seventh Appointment

Arch wire 22 dimensions are stepped up to 0.018 mm×0.025 mm stainless steel alloy as necessary. Stainless steel "figure-eight" ligation is used between the brackets 20 of the first biscuspid to first biscuspid to maintain space closure. All rotations are religated with twisted elastic ligatures. Sliding arch mechanics with elastic chains are utilized to direct further corrective tooth movement, initiate current rotations, space closure and make midline corrections.

Eighth Appointment

Religation and implementation of sliding arch corrective mechanics are carried out at this time. The arch wire 22 dimension is stepped up to 0.018 mm×0.025 mm stainless steel.

Ninth Appointment

The arch wires 22 are stepped down to 0.016 mm round stainless steel alloy. Arch wire 22 lengths and the blocked tubes 1 are utilized to maintain appropriate arch length, as described above. Twisted elastic ligature ligation is used to ensure maximum bracket 20 engagement. Ideal esthetic detailing is produced by the final positioning of bends in the maxillary and mandibular arch wires 22.

Tenth Appointment

Additional final positioning bends, and 0.016 mm round stainless steel arch wire 22 placement, are carried out as necessary.

Eleventh Apointment

All brackets 20 are debonded and removed, and all bonding material is removed. Final esthetic recontouring for optimal smile results is carried out. Fixed maxilary and mandibular ligual cuspid resinds and poly-vinyl cord are fabricated and fitted in place. In a perfecting feature, a one hour light-activated tooth whitening procedure is completed, and nightwear trays to augment the whitening procedure are fabricated.

The patient's retainers are examined for stability. Final records, including panoramic x-rays and photographs, are completed. The records are examined for pathology and abnormalities such as root resorbtion.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

Having thus described my invention, what I claim as new and desire to secure by Letters Patent is as follows:

1. A blocked tube used for straightening teeth comprising:
   a base;
   a body attached to the base;
   a channel disposed within the base, the channel being substantially parallel to a bottom end of the base;
   an extension extending from the base, the extension being substantially parallel to the channel; and
   an arm extending upward and substantially perpendicular to the extension and proximate to an end of the channel and acting as a stop for an arch wire passing through the channel.

2. The blocked tube of claim 1, further comprising a hook extending from an upper end of the base opposing the extension.

3. The blocked tube of claim 1, wherein the body and the base are integrally formed and the channel is a bore substantial formed in the integrally formed body and base, the bore is substantially parallel to the bottom end of the base.

4. The blocked tube of claim 1, wherein the body includes a top and sidewalls, the top and sidewalls of the body and an upper surface of the base form the channel.

5. The blocked tube of claim 4, wherein the sidewalls are substantially perpendicular to the upper surface of the base.

6. The blocked tube of claim 5, wherein the sidewalls are slanted with respect to the upper surface of the base.

7. The blocked tube of claim 1, wherein a length of the extension is approximately 0.145 mm.

8. The blocked tube of claim 1, wherein the arm extends beyond an end of the base by approximately 0.050 mm.

9. The blocked tube of claim 1, wherein a length of the arm is approximately equal to the distance between the channel and a bottom end of the base.

10. The blocked tube of claim 1, wherein a length of the arm is greater than the distance between the channel and a bottom end of the base.

11. The blocked tube of claim 1, wherein a length of the arm is less than the distance between the channel and a bottom end of the base.

12. The blocked tube of claim 1, wherein the extension extends from a bottom or top edge of the base and the arm extends upwards or downwards from the extension, respectively.

13. The blocked tube of claim 1, further comprising a second extension extending from an opposing side of the base with respect to the extension, and the arm extends between the extension and the second extension thereby forming a U-shape.

14. A method of straightening teeth using a blocked tube and conventional brackets, the blocked tube including a base having a channel extending therethrough and an L-shaped or U-shaped extension, the L-shaped or U-shaped extension including a blocking wall extending perpendicular to the channel of the base, the method comprising:

mounting the conventional brackets on the teeth to be straightened;
mounting at least two of said blocked tubes to the teeth immediately posterior to the teeth to be straightened on respective sides of a patient's mouth;
ligating arch wires to the conventional brackets and extending the arch wires through the channel of the base of each tube;
cutting the arch wires so that a distal end of the arch wires contact the blocking walls of the blocked tubes; and
adjusting the arch wires so that the distal ends of the arch wires maintain contact with the blocking walls.

15. The method of claim 14, wherein the blocked tubes are mounted to either upper or lower bicuspids.

16. The method of claim 14, further comprising air rotor stripping on the teeth to be straightened prior to mounting the conventional brackets.

17. The method of claim 14, further comprising maintaining an arch length or expanding an arch length of up to approximately 2 mm.

18. The method of claim 14, further comprising increasing the dimensions of the arch wire.

19. The method of claim 18, wherein the dimensions of the arch wire are increased in sequence from 0.0175 mm×0.025 mm nickel-titanium alloy to 0.018 mm×0.025 mm stainless steel, and then decreased to 0.016 mm round stainless steel.

20. The method of claim 14, further comprising:
   implementation of sliding arch corrective mechanics to direct further corrective tooth movement; and
   initiation of current rotations and space closure and midline corrections.

21. The method of claim 14, further comprising removing the arch wires, conventional brackets and blocked tubes after the patient's teeth are straightened.

22. A blocked tube used for straightening teeth comprising:
   a base;
   a body attached to the base;
   a channel disposed within the base, the channel being substantially parallel to a bottom end of the base;
   an extension extending from the base, the extension being substantially parallel to the channel;
   a second extension extending from an opposing side of the base with respect to the extension; and
   an arm extending upward between the extension and the second extension thereby forming a U-shape, the arm being substantially perpendicular to the extension and proximate to an end of the channel.

23. The blocked tube of claim 1, wherein the extension extends from a side of the base and the arm is substantially perpendicular to the side of the base.

* * * * *